(12) United States Patent
Lai et al.

(10) Patent No.: US 7,279,538 B2
(45) Date of Patent: Oct. 9, 2007

(54) AROMATIC-BASED POLYSILOXANE PREPOLYMERS AND OPHTHALMIC DEVICES PRODUCED THEREFROM

(75) Inventors: Yu-Chin Lai, Pittsford, NY (US); Edmond T. Quinn, Rochester, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 272 days.

(21) Appl. No.: 11/096,455

(22) Filed: Apr. 1, 2005

(65) Prior Publication Data

US 2006/0223964 A1    Oct. 5, 2006

(51) Int. Cl.
*C08F 130/08*    (2006.01)
(52) U.S. Cl. .......................... 526/279; 528/32; 528/43
(58) Field of Classification Search .................. 526/279
See application file for complete search history.

(56) References Cited

U.S. PATENT DOCUMENTS 3,996,187 A    12/1976  Travnicek
4,114,993 A *   9/1978  Travnicek ............... 351/160 R
5,266,352 A *  11/1993  Filas et al. ................ 427/163.2
6,121,368 A    9/2000  Heying et al.
6,361,561 B1 *  3/2002  Huo et al. .................. 623/6.56
6,399,734 B1 *  6/2002  Hodd et al. .................... 528/32
6,864,341 B2    3/2005  Lai et al.
7,132,492 B2 * 11/2006  Lai et al. ....................... 528/43
2002/0082691 A1  6/2002  Christ et al.
2003/0130465 A1* 7/2003  Lai et al. ....................... 528/25

FOREIGN PATENT DOCUMENTS

EP    0335312 B1    6/1994
EP    1334991 A1    8/2003

OTHER PUBLICATIONS

Hawley' Condensed Chemical Dictionary, definition of "cross-linking", 2002.*

* cited by examiner

*Primary Examiner*—Margaret G. Moore

(57) ABSTRACT

A polysiloxane comprises diaryl, dialkyl, and arylalkyl siloxane units, and further has at least a functional group. Such polysiloxane can be further copolymerized with an additional monomer to produce polymeric compositions suitable for making ophthalmic devices. The additional monomer can be selected to produce desirable properties for ophthalmic applications, such as high refractive index and/or high elongation.

9 Claims, No Drawings

AROMATIC-BASED POLYSILOXANE PREPOLYMERS AND OPHTHALMIC DEVICES PRODUCED THEREFROM

BACKGROUND OF THE INVENTION

The present invention relates to aromatic-based polysiloxane prepolymers. In particular, the present invention relates to aromatic-based polysiloxane prepolymers capable of reacting with other monomers or prepolymers and ophthalmic devices produced therefrom.

Since the 1940s optical devices in the form of intraocular lens (IOL) implants have been utilized as replacements for diseased or damaged natural ocular lenses. In most cases, an intraocular lens is implanted within an eye at the time of surgically removing the diseased or damaged natural lens, such as for example, in the case of cataracts. For decades, the preferred material for fabricating such intraocular lens implants was poly(methyl methacrylate), which is a rigid, glassy polymer.

Softer, more flexible IOL implants have gained in popularity in more recent years due to their ability to be compressed, folded, rolled, or otherwise deformed. Such softer IOL implants may be deformed prior to insertion thereof through an incision in the cornea of an eye. Following insertion of the IOL in an eye, the IOL returns to its original pre-deformed shape due to the memory characteristics of the soft material. Softer, more flexible IOL implants as just described may be implanted into an eye through an incision that is much smaller, i.e., less than 4.0 mm, than that necessary for more rigid IOLs, i.e., 5.5 to 7.0 mm. A larger incision is necessary for more rigid IOL implants because the lens must be inserted through an incision in the cornea slightly larger than the diameter of the inflexible IOL optic portion. Accordingly, more rigid IOL implants have become less popular in the market since larger incisions have been found to be associated with an increased incidence of postoperative complications, such as induced astigmatism.

With recent advances in small-incision cataract surgery, increased emphasis has been placed on developing soft, foldable materials suitable for use in artificial IOL implants. In general, the materials of current commercial IOLs fall into one of three categories: silicones, hydrophilic acrylics and hydrophobic acrylics.

In general, high water content hydrophilic acrylics, or "hydrogels," have relatively low refractive indices, making them less desirable than other materials with respect to minimal incision size. Low refractive index materials require a thicker IOL optic portion to achieve a given refractive power. Silicone materials can have higher refractive indices than high-water content hydrogels, but, in general, still lower than desirable. Low glass transition temperature hydrophobic acrylic materials are desirable because they typically have a high refractive index. Unfortunately, low glass transition temperature hydrophobic acrylic materials, which contain little or no water initially, may absorb pockets of water in vivo causing light reflections or "glistenings." Furthermore, it may be difficult to achieve ideal folding and unfolding characteristics due to the temperature sensitivity of some acrylic polymers.

Because of the noted shortcomings of current polymeric materials available for use in the manufacture of ophthalmic devices, there still is a continued need for stable, biocompatible polymeric materials having desirable physical characteristics and refractive indices.

SUMMARY OF THE INVENTION

In general, the present invention provides polysiloxane prepolymers comprising diaryl, dialkyl, and arylalkyl siloxane units.

In one aspect, the present invention provides polysiloxane prepolymers comprising diaryl, dialkyl, and arylalkyl siloxane units; and further having at least a functional group.

In another aspect, the functional group is selected from the group consisting of vinyl, allyl, acryloyl, acryloyloxy, methacryloyl, methacryloyloxy, epoxide, isocyanate, isothiocyanate, amino, hydroxyl, alkoxy, mercapto, anhydride, carboxylic, fumaryl, styryl, and combinations thereof.

In still another aspect, the present invention provides a method for making a polysiloxane prepolymer comprising diaryl, dialkyl, and arylalkyl siloxane units; and at least a functional group. The method comprises reacting at least one type of diarylalkoxysilane, at least one type of dialkylalkoxysilane, and at least one type of arylalkylalkoxysilane, and a siloxane containing a functional group.

In still another aspect, the siloxane containing a functional group is a difunctional disiloxane.

In yet another aspect, the present invention provides a polymeric composition comprising a reaction product of the polysiloxane prepolymer and at least another monomer.

In yet another aspect, the present invention provides ophthalmic devices comprising a polymeric composition that comprises a reaction product of the polysiloxane prepolymer and at least another monomer.

Other features and advantages of the present invention will become apparent from the following detailed description and claims.

DETAILED DESCRIPTION OF THE INVENTION

In general, the present invention provides polysiloxane prepolymers comprising diaryl, dialkyl, and arylalkyl siloxane units.

In one aspect, the present invention provides polysiloxane prepolymers comprising diaryl, dialkyl, and arylalkyl siloxane units; and further having at least a functional group.

In another aspect, the functional group is selected from the group consisting of vinyl, allyl, acryloyl, acryloyloxy, methacryloyl, methacryloyloxy, epoxide, isocyanate, isothiocyanate, amino, hydroxyl, alkoxy, mercapto, anhydride, carboxylic, fumaryl, styryl, and combinations thereof.

A polysiloxane prepolymer of the present invention can be represented by Formula (I).

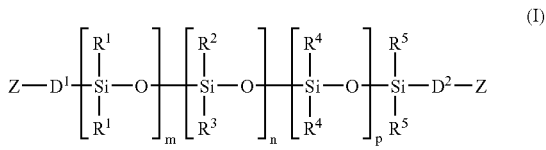

wherein $R^1$ groups are the same or different $C_1$-$C_{10}$ alkyl substituents (such as methyl, ethyl, propyl, butyl, or pentyl) or $C_1$-$C_{10}$ haloalkyl substituents (such as fluoroalkyl, chloroalkyl, or bromoalkyl wherein one or more hydrogen atoms are replaced by halogen atoms); $R^2$ is a $C_1$-$C_{10}$ alkyl susbtituent (such as methyl, ethyl, propyl, butyl, or pentyl) or $C_1$-$C_{10}$ haloalkyl substituents (such as fluoroalkyl, chloroalkyl, or bromoalkyl wherein one or more hydrogen atoms are replaced by halogen atoms); $R^3$ is $C_6$-$C_{36}$ aryl, substituted aryl group, or an aryl group linked or fused with a heterocyclic group; $R^4$ groups are the same or different $C_6$-$C_{36}$ aryl, substituted aryl group, or an aryl group linked or fused with a heterocyclic group; $R^5$ is selected from the group consisting of $R^1$ and $R^4$; $D^1$ and $D^2$ are direct bonds or the same or different saturated or unsaturated straight $C_1$-$C_{10}$ hydrocarbon divalent groups or saturated or unsaturated branched or cyclic $C_3$-$C_{10}$ hydrocarbon divalent groups, with or without one or more heteroatoms in the chain; Z is a functional group selected from the group consisting of vinyl, allyl, acryloyl, acryloyloxy, methacryloyl, methacryloyloxy, epoxide, isocyanate, isothiocyanate, amino, hydroxyl, alkoxy, mercapto, anhydride, carboxylic, fumaryl, styryl, and combinations thereof; and m, n, and p are integers in the range from 1 to, and including, 1000. In one embodiment, 1<m, n, p<500. In still another embodiment, 1<m, n, p<250.

In one aspect, $R^3$ and $R^4$ are independently selected from the group consisting of phenyl, cumenyl, mesityl, tolyl, xylyl, benzyl, benzhydryl, cinnamyl, phenethyl, styryl, trityl, naphthyl, anthryl, phenanthryl, chrysyl, and derivatives thereof. Any one of these group can have one or more substitutents, such as alkyl or heteroalkyl substituents.

In another aspect, Z is selected from the group consisting of vinyl, allyl, acryloyl, acryloyloxy, methacryloyl, methacryloyloxy, epoxide, amino, and hydroxyl.

In one embodiment, Z is the hydroxyl group; $D^1$ and $D^2$ are —$(CH_2)_4$—; $R^1$ and $R^2$ are methyl, $R^3$ and $R^4$ are phenyl group.

In another aspect, the ratio of aryl groups to alkyl groups is such that $(2p+n)/(2m+n) \geq 0.25$.

In another aspect, the polysiloxane prepolymer has a weight average molecular weight in the range from about 1,000 to about 200,000.

In another aspect, polymer compositions comprise a polysiloxane prepolymer and at least another type of monomer. For example, a polymer composition can be made by reacting a polysiloxane prepolymer having hydroxyl end groups of the present invention with a diisocyanate or diacid chloride monomer or phosgene in a selected molar ratio. Another polymer composition can be made by reacting a polysiloxane prepolymer having amino end groups of the present invention with a dicarboxylic acid or dianhydride monomer in a selected molar ratio. Still another polymer composition can be prepared by reacting a polysiloxane prepolymer having epoxide end groups of the present invention with a diamine monomer in a selected molar ratio.

EXAMPLE 1

Preparation of hydroxybutyl-terminated copolymer of dimethylsiloxane, methylphenylsiloxane, and diphenylsiloxane having a phenyl content of about 50 mole percent and having Mn of 2400.

1,3-bis(hydroxybutyl)tetramethyl disiloxane (25 g, 0.09 mole), dimetyldimethoxysilane (81.6 g, 0.68 mole), dimethoxyphenylmethylsilane (123.8 g, 0.68 mole), and diphenyidimethoxysilane (165.9 g, 0.68 mole) were added into a two-liter round bottom flask. Water (34 g) and concentrated hydrochloric acid (9 ml) were added dropwise to the flask. The contents of the flask were refluxed at 60-65° C. for two hours. Methanol was distilled from the contents. Water (36.5 ml) and concentrated hydrochloric acid (36.5 ml) were added to the flask. The contents of the flask were refluxed again for three hour. The contents of the flask were then poured into a separatory funnel. The silicone layer was separated, diluted with 200 ml ether, and extracted once with 100 ml water, twice with 100 ml of 5-percent sodium bicarbonate aqueous solution, and twice with 100 ml water. The final organic layer was dried with magnesium sulfate, and vacuum stripped at 80° C. (at 0.1 mm Hg pressure) to give a crude product. It had a refractive index of 1.53. The crude product was then purified by a Waters preparative size exclusion chromatography ("SEC") using THF (without butylated hydroxy toluene) as solvent to give a purified product. The weight average molecular weight of the purified product should be at least 2400. The refractive index of the product should be at least 1.52.

EXAMPLE 2

Preparation of methacrylate-capped prepolymer using hydroxybutyl-terminated copolymer of dimethylsiloxane, methylphenylsiloxane, and diphenylsiloxane, isophorone diisocyanate and end-capped with 2-hydroxyethyl methacrylate ("HEMA").

A 500-ml round bottom flask equipped with a reflux condenser and nitrogen blanket is charged with isophorone diisocyanate, the hydroxybutyl-terminated copolymer of dimethylsiloxane, methylphenylsiloxane, and diphenylsiloxane from Example 1 in amolar ratio of 3:2, dibutyltin dilaurate (1 percent of the combined weight of polysiloxane and diisocyanate) and methylene chloride (150 ml). The contents are refluxed for about 90 hours. At the end of this period, the isocyanate should decrease to about 30-35 percent (theoretically 33 percent) of the original. The contents of the flask are allowed to cool to ambient temperature. HEMA at a molar ratio of 2/3 of diisocyanate and 1,1'-2-bi-naphthol (5.7 mg) are added to the flask. The contents are continuously stirred for 7 days. At the end of this period, the isocyanate peak disappears from IR spectrum and the reaction is terminated. The product is obtained at quantitative yield after removing the solvent. A methacrylate-capped prepolymer prepared by the method of Example 2 has a general Formula (II), wherein IPDI is the residue of isophorone diisocyanate after the isocyanate groups are removed; and a, b, x, y, and z are positive integers, depending on the molar proportions of isophorone diisocyanate and siloxane monomer units.

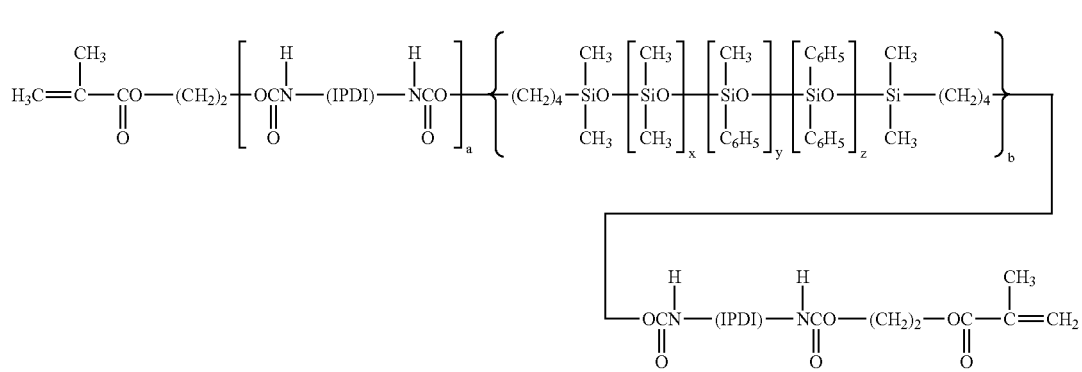

Formula (II)

A polymer comprising a prepolymer of the present invention can have refractive index of about 1.45 or higher. In certain embodiments, the refractive index is in the range from about 1.45 to about 1.55. Refractive index can also tuned by reacting a polysiloxane prepolymer of the present invention with another type of monomer having selected structure, for example, one that has one or more aromatic moieties. Such monomer can increase the refractive index from that of the prepolymer.

Polymeric compositions can be made by copolymerization of a polysiloxane prepolymer of the present invention with one or more aromatic monomers, alkyl monomers, hydrophilic monomers, or combinations thereof. Such a polymeric composition can have a glass transition temperature ("$T_g$") less than about 60° C., particularly less than about 40° C.

Examples of aromatic monomers useful in the production of polymeric compositions of the present invention include for example but are not limited to acrylate, methacrylate, acrylamide and methacrylamide, each with $C_{6-36}$ aromatic substituents. More specific examples of such aromatic monomers include but are not limited to phenyl acrylate, phenyl methacrylate, phenyl acrylamide, benzyl acrylate, benzyl acrylamide, phenylethyl acrylate, phenyl methacrylamide, phenylethyl methacrylate and benzyl methacrylate.

Non-limiting examples of alkyl monomers useful in the production of polymeric compositions of the present invention include for example but are not limited to $C_{1-20}$ alkyl acrylate, $C_{1-20}$ alkyl methacrylate, $C_{5-20}$ alkyl acrylamide, and $C_{1-20}$ alkyl methacrylamide. More specific examples of such alkyl monomers include for example but are not limited to methyl acrylate, ethyl acrylate, n-propyl acrylate, n-butyl acrylate, n-hexyl acrylate, n-octyl acrylate, 2-ethylhexyl acrylate, n-propyl methacrylate, n-butyl methacrylate, n-hexyl methacrylate, n-octyl methacrylate, 2-ethylhexyl methacrylate and n-octyl acrylamide.

Non-limiting examples of hydrophilic monomers useful in the production of polymeric compositions of the present invention include for example but are not limited to N,N-dimethyl acrylamide, N-vinylpyrrolidone, 2-hydroxyethyl methacrylate, glycerol methacrylate, 2-hydroxyethyl acrylate, acrylamide, N-methyl acrylamide, acrylic acid, and methacrylic acid.

In one embodiment, a polymeric composition also comprises units of a cross-linking agent. One class of such cross-linking monomers is the group of compounds having ethylenically unsaturated terminal groups having more than one unsaturated group. Suitable cross-linking agents include, for example, ethylene glycol dimethacrylate ("EGDMA"); diethylene glycol dimethacrylate; ethylene glycol diacrylate; allyl methacrylates; allyl acrylates; 1,3-propanediol dimethacrylate; 1,3-propanediol diacrylate; 1,6-hexanediol dimethacrylate; 1,6-hexanediol diacrylate; 1,4-butanediol dimethacrylate; 1,4-butanediol diacrylate; trimethylolpropane trimethacrylate ("TMPTMA"); glycerol trimethacrylate; polyethyleneoxide mono- and diacrylates; and the like. The amount of cross-linking agent generally is less than about 10 percent (by weight) of the weight of the polymeric composition. In some embodiments, the amount of cross-linking agent is less than about 5 percent (by weight).

In another embodiment, a polymeric composition comprises a polysiloxane prepolymer as disclosed above, at least an additional monomer, and a ultraviolet ("UV") radiation absorber. Non-limiting example of suitable UV absorbers are β-(4-benzotriazoyl-3-hydroxyphenoxy)ethyl acrylate; 4-(2-acryloxyethoxy)-2-hydroxybenzophenone; 4-methacryloxy-2-hydroxybenzophenone; 2-(2'-methacryloxy-5'-methylphenyl)benzotriazole; 2-(2'-hydroxy-5'-methacryoxyethylphenyl)-benzotriazole; 2-[3'-tert-butyl-2'-hydroxy-5'-(3"-methacryloyloxypropyl)phenyl]-5-chlorobenzotriazole; 2-[3'-tert-butyl-5'-(3"-dimethylvinylsilypropoxy)-2'-hydroxyphenyl]-5-methoxybenzotriazole; 2-(3'-allyl-2'-hydroxy-5'-methylphenyl)benzotriazole; 2-[3'-tert-butyl-2'-hydroxy-5'-(3"-methacryloyloxypropoxy)phenyl]-5-methoxybenzotriazole; and 2-[3'-tert-butyl-2'-hydroxy-5'-(3"-methacryloyloxypropoxy)phenyl]-5-chlorobenzotriazole.

In another aspect, a polymer composition made from a polysiloxane prepolymer of the present invention can have an elongation of 100 percent or higher.

The present invention also provides a method for producing a polysiloxane prepolymer comprising diaryl, dialkyl, and alkylaryl siloxane units, and at least a functional group. The method comprises reacting at least one type of diarylalkoxysilane, at least one type of dialkylalkoxysilane, and at least one type of arylalkylalkoxysilane, and a siloxane containing a functional group. In one aspect, the alkyl, aryl, and arylalkyl groups are independently selected from the appropriate $R^1$, $R^2$, $R^3$, and $R^4$, disclosed above, at a temperature and for a time sufficient to produce the polysiloxane prepolymer. The functional group can be selected from the functional groups disclosed above. In one embodiment, the alkyl, aryl, and arylalkyl groups are methyl, phenyl, phenylmethyl, respectively.

In one aspect, a method for producing a polymeric composition comprises: (a) reacting at least one type of diarylalkoxysilane, at least one type of dialkylalkoxysilane, and at least one type of arylalkylalkoxysilane, and a siloxane containing a functional group, wherein the alkyl, aryl, and arylalkyl groups are independently selected from the appropriate $R^1$, $R^2$, $R^3$, and $R^4$ disclosed above, and the functional group is selected from the functional groups disclosed above, at a first temperature and for a first time sufficient to produce the polysiloxane prepolymer; (b) reacting the polysiloxane prepolymer with at least an additional monomer having a complementary functional group to the functional group of the polysiloxane prepolymer, at a second temperature and for a second time sufficient to produce the polymeric composition. The first and second temperatures can be in the range from about ambient temperature to about 120° C. The first and the second times can be in the range from about 1 minute to about 10 days, preferably from about 10 minutes to about 100 hours.

In another aspect, the method further comprises adding a cross-linking agent to the reaction mixture of step (a). The cross-linking agent can be selected from the group of cross-linking agents disclosed above.

In still another aspect, the method further comprises adding a polymerizable UV absorber to the reaction mixture of step (a) or (b). The polymerizable UV absorber can be selected from the group of UV absorbers disclosed above.

A formulation comprising a polysiloxane prepolymer, as disclosed above, can be used to make almost any type of ophthalmic devices, such as contact lenses, corneal rings, corneal inlays, keratoprostheses, and IOLs. In one aspect, the formulation is used to make IOLs that are soft, elongable, and capable of being rolled or folded and inserted through a relative small incision in the eye, such as an incision of less than about 3.5 mm.

A method of making an ophthalmic device comprises: (a) providing a mixture comprising a functionally-capped polysiloxane prepolymer and a monomer; (b) disposing the mixture in a mold cavity, which forms a shape of the ophthalmic device; and (c) curing the mixture under a condition and for a time sufficient to form the ophthalmic device. In one aspect, the mixture also comprises a cross-linking agent, or a polymerization initiator, or both. The polymerization initiator can be a thermal polymerization initiator or a photoinitiator; preferably, a thermal polymerization initiator. The curing can be carried out at an elevated temperature such as in the range from ambient temperature to about 120° C. In some embodiments, the curing is carried out at a temperature from slightly higher than ambient temperature to about 100° C. A time from about 1 minute to about 48 hours is typically adequate for the curing.

Another method of making an ophthalmic device comprises: (a) providing a mixture comprising a functionally-capped polysiloxane prepolymer and a monomer; (b) casting the mixture under a condition and for a time sufficient to form a solid block; and (c) shaping the block into the ophthalmic device. In one aspect, the mixture also comprises a cross-linking agent, or a polymerization initiator, or both. The polymerization initiator is preferably a thermal polymerization initiator. The casting can be carried out at an elevated temperature such as in the range from ambient temperature to about 120° C. In some embodiments, the casting is carried out at a temperature from slightly higher than ambient temperature to about 100° C. A time from about 1 minute to about 48 hours is typically adequate for the polymerization. The shaping can comprise cutting the solid block into wafers, and lathing or machining the wafers into the shape of the final ophthalmic device.

Ophthalmic medical devices manufactured using polymeric materials of the present invention are used as customary in the field of ophthalmology. For example, in a surgical cataract procedure, an incision is placed in the cornea of an eye. Through the corneal incision the cataractous natural lens of the eye is removed (aphakic application) and an IOL is inserted into the anterior chamber, posterior chamber or lens capsule of the eye prior to closing the incision. However, the subject ophthalmic devices may likewise be used in accordance with other surgical procedures known to those skilled in the field of ophthalmology.

While specific embodiments of the present invention have been described in the foregoing, it will be appreciated by those skilled in the art that many equivalents, modifications, substitutions, and variations may be made thereto without departing from the spirit and scope of the invention as defined in the appended claims.

What is claimed is:

1. A polymeric composition comprising a copolymer of a polysiloxane prepolymer, another monomer and units of a cross-linking agent, wherein the polysiloxane prepolymer has a formula of

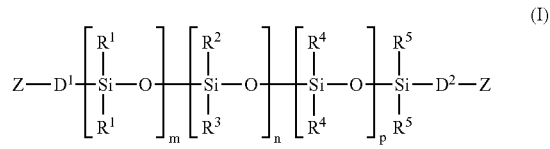

wherein $R^1$ groups are the same or different and are selected from the group consisting of $C_1$-$C_{10}$ alkyl and $C_1$-$C_{10}$ haloalkyl; $R^2$ is selected from the group consisting of $C_1$-$C_{10}$ alkyl and $C_1$-$C_{10}$ haloalkyl; $R^3$ and $R^4$ are independently selected from the group consisting of phenyl, cumenyl, mesityl, tolyl, xylyl, benzyl, benzhydryl, cinnamyl, phenethyl, styryl, trityl, naphthyl, anthryl, phenanthryl, chrysyl, and derivatives thereof; $R^5$ is selected from the group consisting of $R^1$ and $R^4$; $D^1$ and $D^2$ are the same or different and are selected from the group consisting of direct bonds, saturated and unsaturated straight $C_1$-$C_{10}$ hydrocarbon divalent groups, saturated and unsaturated branched $C_3$-$C_{10}$ hydrocarbon divalent groups, cyclic $C_3$-$C_{10}$ hydrocarbon divalent groups, with or without one or more heteroatoms therein; Z is a functional group selected from the group consisting of vinyl, allyl, acryloyl, acryloyloxy, methacryloyl, methacryloyloxy, epoxide, isocyanate, isothiocyanate, amino, hydroxyl, anhydride, carboxylic, and combinations thereof; m, n, and p are integers in the range from 1 to, and including, 1000; and $(2p+n)/(2m+n) \geq 0.25$; and wherein said another monomer is selected from the group consisting of aromatic monomers, alkyl monomers, hydrophilic monomers, or combinations thereof.

2. The polymeric composition of claim 1, wherein the aromatic monomers are selected from the group consisting of phenyl acrylate, phenyl methacrylate, phenyl acrylamide, benzyl acrylate, benzyl acrylamide, phenylethyl acrylate, phenyl methacrylamide, phenylethyl methacrylate and benzyl methacrylate.

3. The polymeric composition of claim 1, wherein the alkyl monomers are selected from the group consisting of methyl acrylate, ethyl acrylate, n-propyl acrylate, n-butyl acrylate, n-hexyl acrylate, n-octyl acrylate, 2-ethylhexyl acrylate, n-propyl methacrylate, n-butyl methacrylate, n-hexyl methacrylate, n-octyl methacrylate, 2-ethylhexyl methacrylate and n-octyl acrylamide.

4. The polymeric composition of claim 1, wherein the hydrophilic monomers are selected from the group consisting of N,N-dimethyl acrylamide, N-vinylpyrrolidone, 2-hydroxyethyl methacrylate, glycerol methacrylate, 2-hydroxyethyl acrylate, acrylamide, N-methyl acrylamide, acrylic acid, and methacrylic acid.

5. The polymeric composition of claim 1, wherein the cross-linking agent is selected from the group consisting of ethylene glycol dimethacrylate ("EGDMA"); diethylene glycol dimethacrylate; ethylene glycol diacrylate; allyl methacrylates; allyl acrylates; 1,3-propanediol dimethacrylate; 1,3-propanediol diacrylate; 1,6-hexanediol dimethacrylate; 1,6-hexanediol diacrylate; 1,4-butanediol dimethacrylate; 1,4-butanediol diacrylate; trimethylolpropane trimethacrylate ("TMPTMA"); glycerol trimethacrylate; and polyethyleneoxide diacrylates.

6. The polymeric composition of claim 1, wherein the copolymer further comprises a UV absorber selected from the group consisting of β-(4-benzotriazoyl-3-hydroxyphenoxy)ethyl acrylate; 4-(2-acryloxyethoxy)-2-hydroxybenzophenone; 4-methacryloxy-2-hydroxybenzophenone; 2-(2'-methacryloxy-5'-methylphenyl)benzotriazole; 2-(2'-hydroxy-5'-methacryoxyethylphenyl)-benzotriazole; 2-[3'-tert-butyl-2'-hydroxy-5'-(3''-methacryloyloxypropyl)phenyl]-5-chlorobenzotriazole; 2-[3'-tert-butyl-5'-(3''-dimethylvinylsilylpropoxy)-2'-hydroxyphenyl]-5-methoxybenzotriazole; 2-(3'-allyl-2'-hydroxy-5'-methylphenyl)benzotriazole; 2-[3'-tert-butyl-2'-hydroxy-5'-(3''-methacryloyloxypropoxy)phenyl]-5-methoxybenzotriazole; and 2-[3'-tert-butyl-2'-hydroxy-5'-(3''-methacryloyloxypropoxy)phenyl]-5-chlorobenzotriazole.

7. An ophthalmic device comprising a polymeric composition of claim 1.

8. A method for making a siloxane-containing polymeric composition, the method comprising:
producing a polysiloxane prepolymer by reacting at least one diarylalkoxy silane, at least one dialkylalkoxy silane, at least one arylalkylalkoxy silane, and at least one siloxane containing a functional group, wherein the polysiloxane prepolymer has a formula of

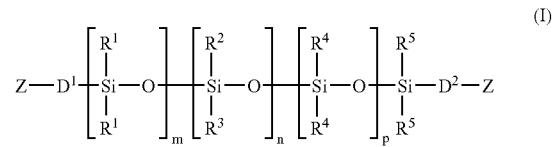

wherein $R^1$ groups are the same or different and are selected from the group consisting of $C_1$-$C_{10}$ alkyl and $C_1$-$C_{10}$ haloalkyl; $R^2$ is selected from the group consisting of $C_1$-$C_{10}$ alkyl and $C_1$-$C_{10}$ haloalkyl; $R^3$ and $R^4$ are independently selected from the group consisting of phenyl, cumenyl, mesityl, tolyl, xylyl, benzyl, benzhydryl, cinnamyl, phenethyl, styryl, trityl, naphthyl, anthryl, phenanthryl, chrysyl, and derivatives thereof; $R^5$ selected from the group consisting of $R^1$ and $R^4$; $D^1$ and $D^2$ are the same or different and are selected from the group consisting of direct bonds, saturated and unsaturated straight $C_1$-$C_{10}$ hydrocarbon divalent groups, saturated and unsaturated branched $C_3$-$C_{10}$ hydrocarbon divalent groups, cyclic $C_3$-$C_{10}$ hydrocarbon divalent groups, with or without one or more heteroatoms therein; Z is a functional group selected from the group consisting of vinyl, allyl, acryloyl, acryloyloxy, methacryloyl, methacryloyloxy, epoxide, isocyanate, isothiocyanate, amino, hydroxyl, anhydride, carboxylic, and combinations thereof; m, n, and p are integers in the range from 1 to, and including, 1000 and $(2p+n)/(2m+n) \geq 0.25$; and reacting the polysiloxane prepolymer with an additional monomer and a crosslink agent at a temperature and for a time sufficient to produce the siloxane-containing polymeric composition.

9. The method of claim 8, wherein the additional monomer is selected from the group consisting of aromatic monomers, alkyl monomers, hydrophilic monomers, or combinations thereof.

* * * * *